US010206846B1

United States Patent
Al-Oboudi

(10) Patent No.: US 10,206,846 B1
(45) Date of Patent: Feb. 19, 2019

(54) STEP FOOT ALIGNING DEVICE

(71) Applicant: Waleed Al-Oboudi, San Diego, CA (US)

(72) Inventor: Waleed Al-Oboudi, San Diego, CA (US)

(*) Notice: Subject to any disclaimer, the term of this patent is extended or adjusted under 35 U.S.C. 154(b) by 215 days.

(21) Appl. No.: 14/636,046

(22) Filed: Mar. 2, 2015

Related U.S. Application Data

(60) Provisional application No. 61/946,584, filed on Feb. 28, 2014.

(51) Int. Cl.
*A61H 3/00* (2006.01)
*A61F 5/01* (2006.01)

(52) U.S. Cl.
CPC .............. *A61H 3/00* (2013.01); *A61F 5/0111* (2013.01); *A61F 5/0113* (2013.01); *A61H 2003/007* (2013.01)

(58) Field of Classification Search
CPC ... A61H 3/00; A61H 2003/007; A61F 5/0102; A61F 5/0111; A61F 5/0113; A61F 5/0127; A61F 5/0585; A61F 5/019; A47D 13/04; A43C 19/00; A43C 13/06; A43C 13/08; A43B 7/24; A43B 7/19; A43B 7/20; A43B 23/22; A43B 13/184
See application file for complete search history.

(56) References Cited

U.S. PATENT DOCUMENTS

| | | | | | |
|---|---|---|---|---|---|
| 3,844,054 | A * | 10/1974 | Morris | ................. | A43B 23/227 36/1 |
| 5,215,508 | A * | 6/1993 | Bastow | ................. | A63B 23/08 482/112 |
| 5,490,831 | A * | 2/1996 | Myers | ................. | A61F 5/0102 602/16 |
| 6,557,271 | B1 * | 5/2003 | Weaver, III | ......... | A43B 3/0063 36/144 |
| 6,634,656 | B1 * | 10/2003 | Gervasoni | ............ | A43B 5/1633 280/11.223 |
| 7,175,187 | B2 * | 2/2007 | Lyden | ................. | A63C 17/004 280/11.206 |
| 8,776,402 | B2 * | 7/2014 | Cromer, Jr. | ........... | A61F 5/0111 36/112 |
| 2006/0020233 | A1 * | 1/2006 | Bremer | ................. | A61F 5/0111 602/23 |
| 2008/0256831 | A1 * | 10/2008 | Maiores | ............... | A43B 5/1633 36/115 |

(Continued)

OTHER PUBLICATIONS

Knob—Definition. (n.d.). Retrieved May 1, 2017, from https://www.merriam-webster.com/dictionary/knob.*

(Continued)

*Primary Examiner* — Alireza Nia
*Assistant Examiner* — Rachel Berezik
(74) *Attorney, Agent, or Firm* — Knobbe Martens Olson & Bear LLP

(57) ABSTRACT

A device for correcting foot alignment is provided. The device includes a base configured to receive at least a portion of a person's foot and an elongate alignment member extending from the lateral side of the base. The elongate alignment member comprises a bracket and a stopper extending outwardly from the bracket. The alignment member prevents the person's foot from rotating outwardly when the person is wearing the device.

8 Claims, 3 Drawing Sheets

(56) References Cited

U.S. PATENT DOCUMENTS

2008/0307674 A1* 12/2008 Dean .................. A43B 3/0031
36/89
2014/0298679 A1* 10/2014 Brun del Re .......... A63B 25/10
36/27

OTHER PUBLICATIONS

Level. The Free Dictionary. adjective, definition 3a, https://www.thefreedictionary.com/level.*
Knob. Merriam Webster Online Dictionary. https://www.merriam-webster.com/dictionary/knob. p. 1 definition 1 b.*

* cited by examiner

STEP FOOT ALIGNING DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The invention generally relates to orthotic devices, and more particularly, to a device that helps correct foot alignment in rehabilitating patients.

Description of the Related Art

A patient's walking ability can be impaired due to stroke, brain injury or other illnesses. It is often difficult for such patients to properly align the foot when walking. Instead of pointing the foot forward, the patient tends to rotate the foot outward at the end of a stepping through. This in turn may exert excessive strain on the hips or knee. Thus, there is a need for a device that helps correct foot alignment in rehabilitating patients.

SUMMARY OF THE INVENTION

The systems, methods and devices described herein have innovative aspects, no single one of which is indispensable or solely responsible for their desirable attributes. Without limiting the scope of the claims, some of the advantageous features will now be summarized.

In some embodiments, the foot aligning device comprises a base having a lateral side and a medial side, and configured to receive at least a portion of a person's foot or shoe. The device further comprises an elongate alignment member, wherein the elongate alignment member extends from the lateral side of the base and comprises a stopper that is attached to a distal end of the elongate alignment member. The stopper is configured to prevent the person's foot from rotating outwardly when the base is attached to the person's foot. In some implementations, the elongate alignment member is a bracket connected to a knob.

In some embodiments, the foot aligning device may comprise a base, one or more walls, an alignment member such as a knob, a bracket, and one or more straps. The one or more walls may be disposed on at least one edge of the base. The knob may be disposed adjacent or proximate the base and may be near a back edge of the base. The knob may be connected to or attached to the base or other part of the device by a bracket. One or more straps may be disposed on the device, and may be attached to the one or more walls, the base, or other part of the device. The straps may be configured to help secure at least part of the foot aligning device to the user's foot or shoe. In some embodiments, the bottom surface of the knob is below the bottom surface of the base. In some embodiments the bottom surface of the knob is level with the bottom surface of the base or higher than the bottom surface of the base. In some embodiments, at least part of the knob may be disposed below at least part of the base. The device may be configured such that the length of the base is approximately ⅔ the length of a user shoe, or may be configured such that the length of the base is between ⅓ the length of the user's shoe and the entire length of the users shoe. In some embodiments, the length of the base may be longer than the length of the user's shoe.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Like reference numbers and designations in the various drawings indicate like elements. Not all of the elements of the drawings are in to scale relate to other drawings and the comparative size of one element relative to another element in the drawings is not necessarily indicative of the relative sizes of the elements in one or more embodiments.

DETAILED DESCRIPTION OF THE PREFERRED EMBODIMENT

Figure 1:
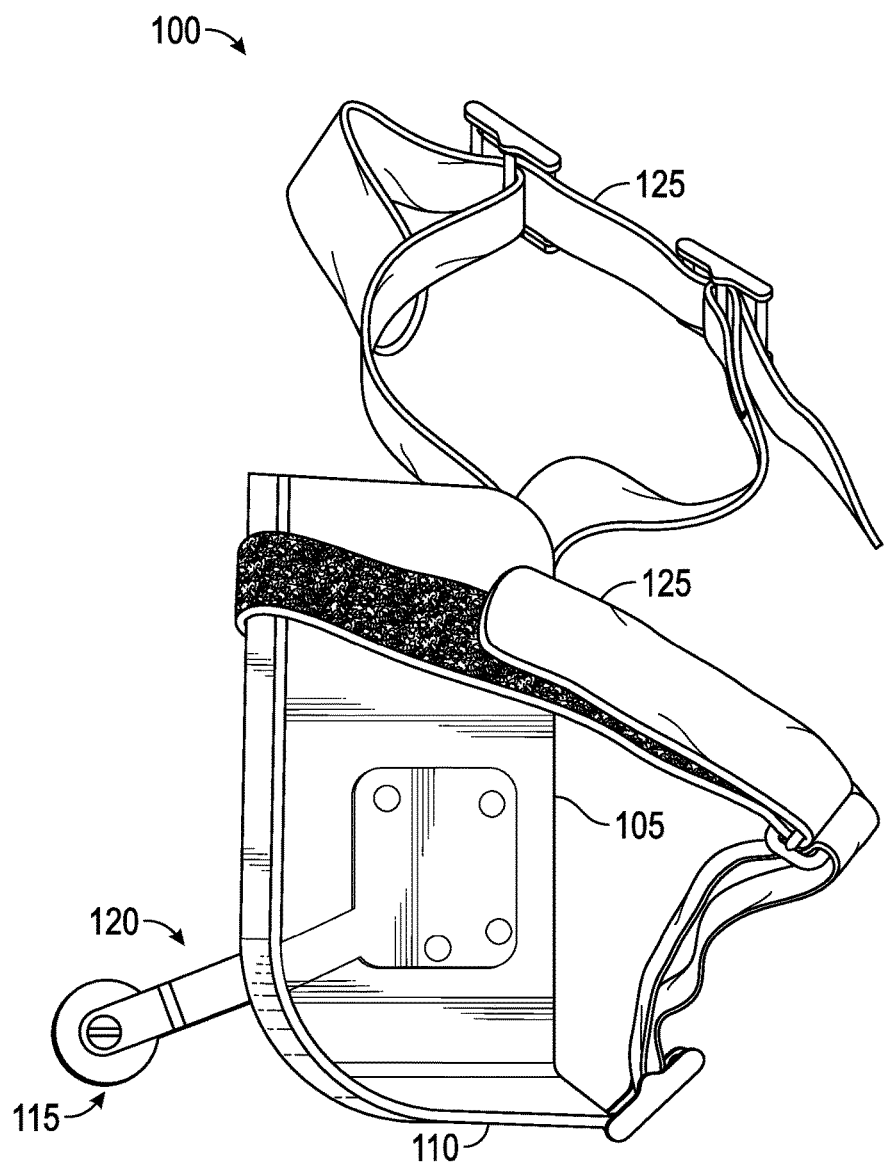
FIG. 1 illustrates a top view of an embodiment of a step foot aligning device.

In the following detailed description, reference is made to the accompanying drawings, which form a part of the present disclosure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure. For example, a system or device may be implemented or a method may be practiced using any number of the aspects set forth herein. In addition, such a system or device may be implemented or such a method may be practiced using other structure, functionality, or structure and functionality in addition to or other than one or more of the aspects set forth herein. Elements that are described as "connected," "engaged," "attached," or similarly described, shall include being directly and/or indirectly connected, engaged, attached, etc. Alterations and further modifications of the inventive features illustrated herein, and additional applications of the principles of the inventions as illustrated herein, which would occur to one skilled in the art and having possession of this disclosure, are to be considered within the scope of the invention.

Descriptions of unnecessary parts or elements may be omitted for clarity and conciseness, and like reference numerals refer to like elements throughout. In the drawings, the size and thickness of layers and regions may be exaggerated for clarity and convenience.

Features of the present disclosure will become more fully apparent from the following description, taken in conjunction with the accompanying drawings. It will be understood these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description" one will understand how illustrated features serve to explain certain principles of the present disclosure.

Figure 2:
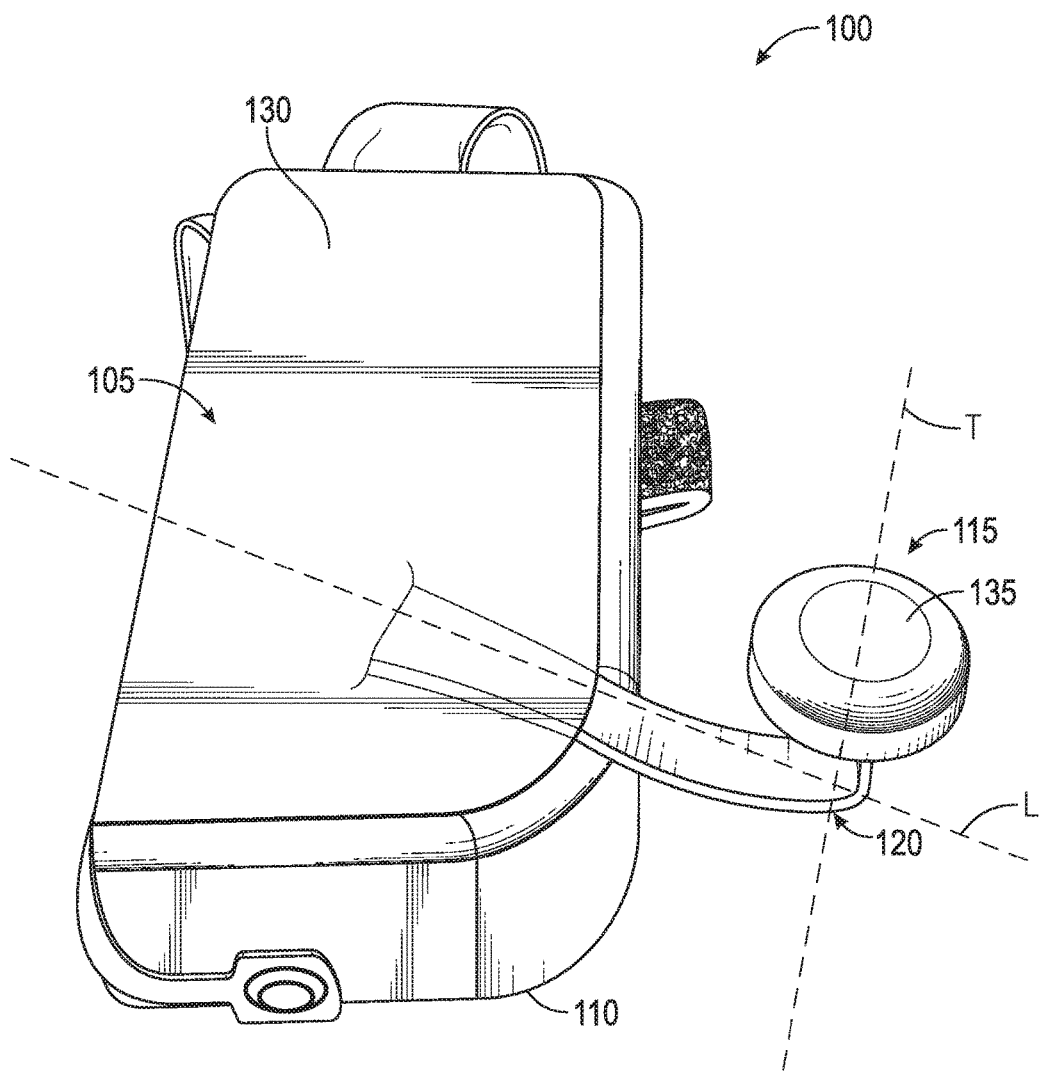
FIG. 2 illustrates a bottom perspective view of an embodiment of a step foot aligning device.

As shown in FIGS. 1 and 2, in some embodiments, the foot aligning device 100 may comprise a base 105, one or more walls 110, an alignment member 115, a bracket 120, and one or more straps 125. The walls 110 may be attached to the base 105 and may extend upward from the base 105. The bracket 120 may extend laterally from the base 105 from between zero to several inches, and may attach to an alignment member 115. The alignment member 115 can be in the form of a knob or stopper. In some implementations, the alignment member 115 comprises a knob that may be approximately 1 inch across but may be larger or smaller in different embodiments. The one or more straps 125 may attach to part of the base 105 and/or walls 110 and may be configured to engage a user's foot, ankle, or shoe.

The foot aligning device 100 may be configured to attach to a user's foot or shoe, specifically to the bottom of a user's foot or shoe. The length of the base 105 may be such that it is approximately ⅔ the length of a user's shoe. However, the length of the base 105 may be greater or shorter depending on the specific application, and the scope of the invention is not limited by the length of the device 100. In some embodiments, the length of the base 105 being two thirds the length of the user's shoe may be beneficial to the user because it may allow the user to engage in a more natural walking motion. The one or more straps 125 may be configured to go over the top of the user's foot and may be configured to go around the ankle or back of the user's foot. The straps 125 may comprise one or more attachment devices such as Velcro or a buckle. The knob 115 may connect to the bracket 120 which may connect to the base 105 of the foot aligning device 100. The knob 115 may comprise a bottom surface that may be disposed elevationally below or lower than a bottom surface of the base 105. The knob 115 may be located below the base 105, or may be laterally adjacent the base 105 by one or more inches. The knob 115 may be generally located proximate the back section of the base 105.

In some embodiments, to use the foot aligning device 100, the foot aligning device 100 may be attached to a user's foot. The user may perform a walking motion using the foot aligning device 100. The user may use the foot aligning device 100 for a period of minutes, hours, days, or a different period of time. The user may use the device 100 continuously, or for various periods of time intermittently. For instance the user may use the device 100 continuously for a period of time such as several days. Or, the user may use the foot aligning device 100 for minutes or hours at a time each day. The user may also use the device for different amounts or intervals of time, and the scope of the invention is not limited by the time periods for which the device 100 is used.

The foot aligning device 100 may be configured to help align a user's foot during the stepping motion. For instance, prior to use, when a user steps during a walking motion, instead of the foot pointing forward, the foot may point outward to the side as the user completes a step and places his foot upon the ground. A user whose foot is not aligned during the stepping motion may benefit from the device. For instance, a user whose foot is turned outward when he steps may benefit from his foot being more aligned, such that the foot is not turned outward (or turned outward to a lesser degree) during the stepping motion. A foot that is turned outward during the stepping motion may exert excessive strain on at least the person's hip and/or knee. The foot aligning device 100 may help rotate the user's foot during the stepping motion, and may help train the user's foot, ankle, hip, and or brain to step without an excessively outturned foot.

Once the foot aligning device 100 is attached to the user's foot, the user may generally walk using his walking motion. When the user places his foot forward and is about to place his heel on the ground, the knob 115 may contact the ground before the user's heel contacts the ground. Once the knob 115 contacts the ground, the user's foot may naturally rotate inward such that when the user's heel contacts the ground, the user's foot is more properly aligned as compared to the alignment of the user's foot before using the foot aligning device 100. In some embodiments, the user may walk using his normal walking motion, and the foot aligning device 100 may rotate the foot during the walking motion into the correct position or a more beneficial position. If both of the user's feet are not aligned during the walking motion, then the user may benefit from using a foot aligning device 100 on each of his feet. The user may desire to use an aligning device 100 on one foot at a time, or he may desire to use two foot aligning devices 100, one on each foot, simultaneously.

In some embodiments, the knob 115 and/or the bracket 120 may be adjustable as compared to the base portion 105. For instance, the knob 115 and/or the bracket 120 may be adjusted so that the bottom surface of the knob 115 is higher or lower as compared to the bottom surface of the base 105. In some embodiments, the knob 115 may be closer to or further away laterally from the base 105, or may be further forward or further back as compared to the back of the base 105. For instance, the knob 115 may be right next to the side of the base 105, may be at least partially underneath the base 105, or may be disposed several inches to the side of the base 105. The knob 115 may be aligned with the back edge of the base 105, forward from the back edge of the base 105, or further back than the back edge of the base 105. In some embodiments, the knob 115 is disposed approximately 2 inches to the side of the base 105 and is approximately level with the back edge of the base 105.

The bracket extends laterally away from the base in a longitudinal direction. The stopper member is attached to the bracket. A surface of the stopper member has a round shape wherein a line normal to the surface and passing through a center of the round shape is transverse to the longitudinal direction.

The walls 110 may be disposed at one or more edges of the base 105 and may elevate above the base 105 from between zero and several inches. The walls 105 may be disposed on the outside edge of the base 105 at the rear edge of the base 105 such that when the user steps forward and the knob 115 contacts the ground, at least part of the user's foot may contact a wall 110 on the side of the base 105 and a wall 110 on the rear of the base 105. In some embodiments, during the walking motion when the knob 115 contacts the ground, a wall 110 on the side of the base 105 and a wall 110 on the rear the base 105 may support or cradle at least part of the user's foot. The one or more walls 110 may act to at least partially secure the foot or shoe to the device 100 such that the one or more walls 110 may at least partially prevent the user's foot or shoe from moving laterally in various directions. In some embodiments, more or fewer walls 110 may be present, depending on the configuration desired. The bottom surface of the base 105 may comprise a gripping surface 130, which may provide a more stable interaction between the bottom of the base 105 and the ground or floor on which the user is walking. Additionally the bottom surface of the knob 115 may comprise a gripping surface 135 such that when the user performs a walking motion and engages the knob 115 with the ground, the knob 115 does not substantially move laterally on the ground during the walking movement.

The base 105 and/or walls 110 may comprise a metal or plastic or other material that is structurally sufficient to support at least part of the user's weight during the walking motion. The one or more straps 125 may comprise nylon straps, and may be about 1 inch in width; however, the straps 125 may be wider or narrower. The knob 115 and bracket 120 may comprise a plastic or metal, or other various materials. The gripping surface 130, 135 on the bottom surface of the knob 115 and/or the base 105 may comprise a rubber, silicone, or other material that may provide some measure of resistance to slipping on the ground.

Figure 3:
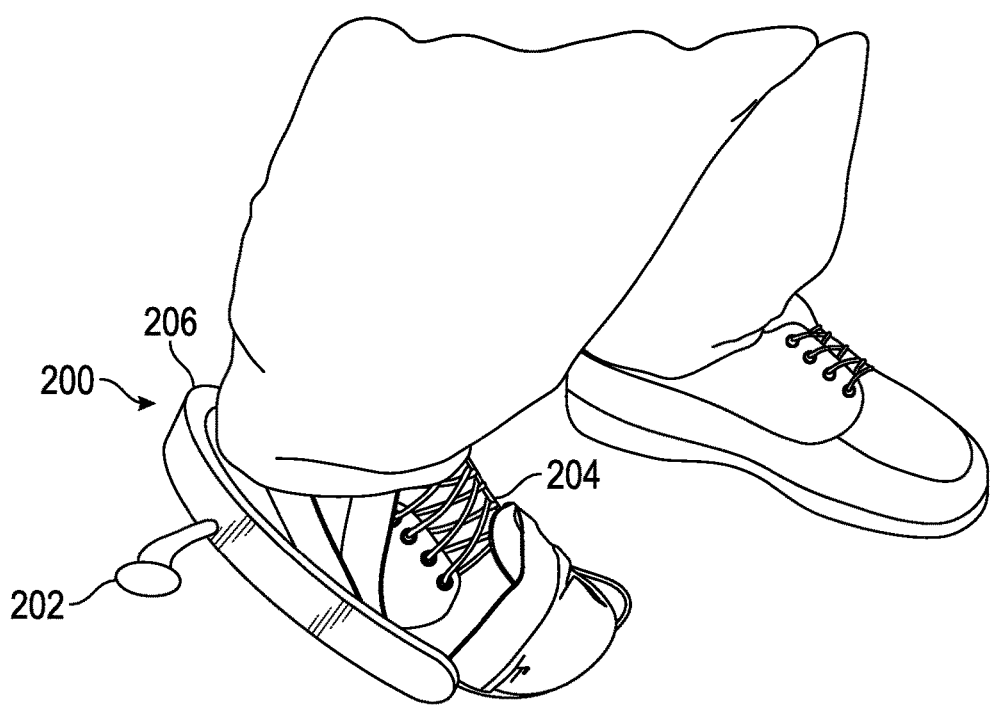
FIG. 3 illustrates a person wearing a step foot aligning device according to one preferred embodiment.

FIG. 3 illustrates a method in which a foot aligning device 200 of a preferred embodiment can be used to correct the alignment of a person's step. As shown in FIG. 3, in use, at least a portion the person's shoe 204 is seated in the device 200 in a manner such that the heel of the shoe is positioned adjacent a rear vertical wall 206 and an alignment member 202 extends laterally outward from the lateral side of the person's foot. The alignment member 202 helps to correct the position of the person's foot by serving as a stopper that inhibits the foot from rotating or pointing outwardly.

Terminology: Additional Embodiments

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of the device as implemented.

Certain features that are described in this specification in the context of separate implementations also can be implemented in combination in a single implementation. Conversely, various features that are described in the context of a single implementation also can be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

In describing the present technology, the following terminology may have been used: The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" means quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3 and 4 and sub-ranges such as 1-3, 2-4 and 3-5, etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Conjunctions, such as "and," "or" are used interchangeably and are intended to encompass any one element, combination, or entirety of elements to which the conjunction refers.

What is claimed is:

1. A foot alignment device, comprising:
a base configured to receive at least a portion of a person's foot, said base comprising a wall having a lateral side and a medial side that faces away from the lateral side, wherein in use the medial side of the wall is configured to face a lateral side of a foot wearing the device;
a bracket extending laterally away from the base along a longitudinal direction; and
a stopper member attached to the bracket, a surface of the stopper member having a round shape, wherein a line normal to the surface and passing through a center of the round shape is transverse to the longitudinal direction.

2. The foot alignment device of claim 1 wherein the stopper member is a knob.

3. The foot alignment device of claim 1, wherein the bracket is bent downwardly from the base.

4. The foot alignment device of claim 3, wherein a lower surface of the stopper member is disposed elevationally below a lower surface of the base.

5. The foot alignment device of claim 1, wherein the stopper member is configured to contact the ground before a heel of a user during a walking motion of the user.

6. The foot alignment device of claim 1, wherein a length of the base is approximately ⅔ a length of a shoe of a user wearing the foot alignment device.

7. The foot alignment device of claim 1, wherein the bracket extends the stopper member approximately 2 inches away from the base in the longitudinal direction.

8. The foot alignment device of claim 1, wherein the stopper member comprises a gripping surface configured to contact the ground and limit a lateral movement of the stopper member during a walking motion of a user wearing the foot alignment device.

* * * * *